United States Patent [19]

Coxon et al.

[11] Patent Number: 5,665,967
[45] Date of Patent: Sep. 9, 1997

[54] APPARATUS AND METHOD FOR SURFACE ANALYSIS

[75] Inventors: Peter A. Coxon, Buxted; Bruce J. McIntosh, East Grinstead, both of England

[73] Assignee: Thermo Instrument Systems Inc., Sunnyvale, Calif.

[21] Appl. No.: 653,390

[22] Filed: May 24, 1996

[30] Foreign Application Priority Data

May 26, 1995 [GB] United Kingdom .................. 9510699

[51] Int. Cl.$^6$ ........................................... H01J 49/40
[52] U.S. Cl. ........................................ 250/287; 250/305
[58] Field of Search ................................. 250/287, 286, 250/281, 282, 305, 310

[56] References Cited

U.S. PATENT DOCUMENTS

| | | | |
|---|---|---|---|
| 3,576,992 | 5/1971 | Moorman et al. | 250/287 |
| 4,255,656 | 3/1981 | Barrie et al. | 250/305 |
| 4,774,408 | 9/1988 | Gohlke | 250/287 |
| 4,912,327 | 3/1990 | Waugh | 250/309 |
| 4,945,236 | 7/1990 | Mogami et al. | 250/287 |
| 5,171,987 | 12/1992 | Waldron et al. | 250/287 |

FOREIGN PATENT DOCUMENTS

| | | |
|---|---|---|
| 0 246 841 B1 | 7/1991 | European Pat. Off. . |
| 1405180 | 9/1975 | United Kingdom . |

OTHER PUBLICATIONS

"An Energy/Mass Analyzer With Two Flat Capacitors"—V.V. Zashkvara et al, Sov. Phys. Tech. Phys. 28(2), Feb. 1983.

"Time-of-Flight Mass Analyzers"—H. Wollnik, Mass Spectrometry Reviews, 1993, 12, 89–114.

"The Time-Focusing Principle: A Double-Focusing Design for Time-of-Flight Mass Spectrometers", J.M.B. Bakker, Int. J. Mass Spectrom.Ion Phys. 6(1971) 291–295.

"From X–Ray to Electron Spectroscopy and New Trends", K. Siegbahn, Journal of Electron Spectroscopy and Related Phenomena, 51(1990) 11–36.

"A Combined MXPS/TOF–SIMS Instrument for the Investigation of Plasma–Deposited Polymeric Films" M. Deimel et al, Combined and/or Related Techniques, 593–596, no date.

"Combined Instrument for the On–Line Investigation of Plasma Deposited or Etched Surfaces by Monochromatized X–Ray Photoelectron Spectroscopy and Time–of–Flight Secondary Ion Mass Spectrometry", P.W. Jahn et al, J. Vac Sci. Technol. A 12(3), May–Jun. 1994.

"Dynamics of Resonant Multiphoton Ionization and Dissociation of Nitrogen via the $a^1 \Pi_g$ (v=9) State Probed With a Novel Electron/Ion Time–of–Flight Spectrometer", C. Rose et al, Intern'l Jrnl of Mass Spectrometry and Ion Processes, 113(1992) 81–98.

An Experimental and Theoretical Study of the Transmission Function of a Commercial Hemispherical Electron Energy Analyser, A.E. Hughes, Surface and Interface Analysis, vol. 4, No. 5, 1982.

*Primary Examiner*—Jack I. Berman
*Assistant Examiner*—Kiet T. Nguyen
*Attorney, Agent, or Firm*—Chilton, Alix & Van Kirk

[57] ABSTRACT

An apparatus and a method for the analysis of the surface of a specimen by the techniques of electron energy spectroscopy and secondary ion time-of-flight mass spectrometry. The apparatus provides a substantially conventional electron energy analyzer, typically having hemispherical electrodes. The energy analyzer is used as an ion deflector and in conjunction with a linear drift region and a pulsed primary ion beam gun provides a time-of-flight mass spectrometer having at least first-order time focusing properties. By using the energy analyzer in both techniques a combined instrument is provided at much lower cost than prior combined instruments which comprise different analyzers for the two techniques.

12 Claims, 4 Drawing Sheets

APPARATUS AND METHOD FOR SURFACE ANALYSIS

BACKGROUND OF THE INVENTION

1. Field of the Invention

This invention relates to method of and apparatus for analyzing the composition of the surface of a specimen by electron spectroscopy and by secondary ion mass spectrometry. In particular, it provides an electron energy spectrometer combined with a secondary ion time-of-flight mass spectrometer, and a method by which a known electron energy spectrometer can be used as a secondary ion mass spectrometer.

2. Description of the Prior Art

Secondary ion mass spectroscopy (SIMS) and a variety of electron spectroscopies (e.g., X-ray photoelectron spectroscopy XPS, electron spectroscopy for chemical analysis ESCA, ultraviolet photoelectron spectroscopy UPS, etc) are commonly used for investigating the chemical structure of the surface of a solid specimen. In the former technique a primary beam of radiation impinges on the surface and releases secondary ions which are analyzed by a mass analyzer. In the latter techniques a primary beam of radiation releases from the surface of the specimen electrons whose energy is measured by a charged-particle energy analyzer to yield information about the chemical nature of the surface from which they were emitted.

Typical prior secondary ion mass spectrometers may comprise magnetic sector, quadrupole and time-of-flight mass analyzers, but time-of-flight analyzers are particularly attractive because of their ability to efficiently record a complete mass spectrum from a pulse of ions liberated from a surface.

Typical prior XPS and ESCA instruments comprise a cylindrical mirror analyzer or a part-spherical energy analyzer together with electrostatic or magnetic lenses to collect electrons emitted from the surface and transmit them to the analyzer. Descriptions of this general class of instrument may be found in U.S. Pat. No. 4,255,656 and in Hughes and Phillips, Surface and Interface Analysis, 1982 vol 4 (5) pp 220–226. Many such instruments are also capable of producing an energy-filtered image of the surface. In both SIMS and ESCA surface analysis apparatus, means for causing the emission of electrons and/or ions is also provided. This may comprise X-ray sources, electron sources, ion sources, UV and/or laser light sources. Both instruments also typically incorporate a UHV housing and vacuum system to prevent contamination of the surface under investigation.

In principle, a time-of-flight mass spectrometer for mass-analyzing ions generated by a pulsed ion source need comprise only an extraction or acceleration region, a field-free drift region and an ion detector. Assuming that the spatial separation of the ions in the bunch is minimal and their kinetic energies are equal at the point at which they enter the drift tube, the ions will separate in time according to their mass-to-charge ratios and arrive sequentially at the detector. In practice, however, the mass resolution is seriously reduced by a spread of the kinetic energies of ions in the bunch which results in ions of the same mass-to-charge ratio arriving at the detector at different times. It is known to minimize this problem by time-focusing, in which ions with higher velocities are made to travel a greater distance than slower ions of the same mass-to-charge ratio, thereby causing them to arrive at the detector at the same time.

The process was described in 1968 in U.S. Pat. No. 3,576,992 which teaches that the combination of a linear drift region with a curved drift region results in time focusing if correctly dimensioned. In this patent it is suggested that the curved drift region may comprise electrostatic ion-deflecting plates having a curved construction, typically cylindrical, spherical or toroidal. Many variations of the concept have been subsequently described e.g., Poschenrieder in GB Patent 1,405,180 (1975), Gohlke in U.S. Pat. No. 4,774,408 (1988), Bakker, Int. Journal Mass Spectrom and Ion Phys, 1971 vol 6 pp 291–5, and a review by Wollnik (Mass Spectrom. Rev. 1993, vol 12 pp 89–114).

Rose, Ondrey and Proch (Int. Journal Mass Spectrom. Ion Proc. 1992 vol 113 pp 81–98) teach that an electrostatic lens may be incorporated into a conventional time-of-flight mass spectrometer, resulting in an instrument capable of analyzing the energies of photoelectrons and determining the mass of ions by time-of-flight mass spectrometry. However, the ion/electron source in this instrument is a molecular beam, rather than a solid surface, and the lens comprises a grid and three electrodes disposed along the charged-particle axis. It does not therefore provide the curved drift region necessary to obtain effective time-focusing, as required by U.S. Pat. No. 3,576,992. To the best of the inventor's knowledge there are no other reports of instruments for both electron energy analysis and ion mass-spectroscopy in which the ions and electrons travel substantially along the same path.

Although there is a superficial similarity between the time-of-flight mass spectrometers of U.S. Pat. No. 3,576,992 and GB 1,405,180 and the conventional part-spherical electron energy analyzers frequently used for ESCA and XPS it will be understood that the charged-particle optical theory which determines their geometrical parameters is quite different. In the case of a time-of-flight spectrometer it is necessary to select the length of the linear portions of the flight path in relation to the length of the curved portion so that time-focusing is achieved. In contrast, in the case of an electron energy spectrometer these lengths are determined by the need for the analyzer system to focus electrons as well as disperse them according to their energies. Consequently the dimensions of apparatus suitable for time-of-flight mass spectroscopy will not in general be suitable for use of that apparatus as an electron spectrometer, and v.v. Thus, although an instrument comprising both an electron energy spectrometer for experiments such as XPS and ESCA and a time-of-flight secondary ion mass spectrometer is obviously a very versatile tool for surface analysis, the only reports of instruments incorporating both techniques teach separate mass and electron-energy analyzers fitted on a single vacuum housing, for example, Jahn, Petrat et al., J. Vac. Sci, Technol. 1994 vol A12 (3) p 671–676 and Siegbahn, J. Electron. Spectros. Related Phenom. 1990 vol 51 pp 11–36.

SUMMARY OF THE INVENTION

It is an object of the present invention to provide apparatus for surface analysis which incorporates both electron spectroscopy and time-of-flight mass spectroscopy and which does not require the provision of separate mass and energy analyzers. It is a further object to provide surface analysis apparatus comprising a part-spherical electrode charged-particle energy analyzer which can also be used as a time-focusing time-of-flight ion mass analyzer. It is a yet further object of the invention to provide a method of surface analysis incorporating both electron energy spectroscopy and secondary ion mass spectroscopy wherein the ions and electrons pass through a single electrostatic deflection means which may provide energy analysis of the electrons or form part of the flight path for ions in a time-of-flight mass analyzer.

In accordance with these objectives the invention provides apparatus for the analysis of a surface of a specimen by electron spectroscopy and secondary ion mass spectrometry, said apparatus comprising:

a) irradiation means for irradiating a specimen to cause it to emit electrons from a surface;

b) irradiation means for irradiating a specimen and generating therefrom one or more bunches of secondary ions, the secondary ions in each of said bunches having a spread of initial kinetic energies, and means for accelerating said secondary ions by passing them through a potential gradient;

c) charged-particle detection means for producing an electrical signal indicative of the number of said electrons or said ions which impinge upon it;

d) disposed between said specimen and said charged-particle detection means:

1) one or more linear drift regions which at least some of said electrons, or said ions after passing through said potential gradient, may enter and leave without change in direction and in which ions in each of said bunches separate in time according to their velocities; and 2) charged-particle deflection means which charged-particles enter in one direction and leave in another direction, said deflection means having notional entrance and exit planes disposed such that an energy-dispersed electron image of electrons passing through said entrance plane may be formed in said exit plane, and in which ions of a given mass-to-charge ratio in each of said bunches separate in time by virtue of the faster ions taking longer paths and therefore having longer transit times;

e) charged-particle focusing means for transmitting said electrons or said ions through at least one of said linear drift regions so that at least when electrons are being transmitted a charged-particle image of at least a part of the surface from which said electrons are emitted is formed at said entrance plane;

f) switchable power supply means for supplying electrical potentials to electrodes comprised in said charged-particle deflection means and said charged-particle focusing means to enable them to transmit ions or electrons as required;

g) means, operable when said charged-particle deflection means and said charged-particle focusing means are transmitting ions, for measuring the time taken for each of said ions comprised in said bunches to travel to said charged-particle detection means, thereby determining the mass-to-charge ratio of at least some of the ions emitted from at least a part of said surface;

h) means, operable when said charged-particle deflection means and said charged-particle focusing means are transmitting electrons, for allowing only electrons having a desired range of energies to reach said charged-particle detection means, thereby determining the energy at which at least some of the electrons are emitted from a said specimen;

said apparatus being so arranged that the separation in time of ions having the same mass-to-charge ratio during their passage through said linear drift region, due to said spread in initial kinetic energies, is compensated by the different times taken for ions having the same mass-to-charge ratio but different energies to travel through said charged-particle deflection means along their different paths, so that ions of the same mass-to-charge ratio in each of said bunches arrive at said charged-particle detector at the same time.

The invention therefore provides a combined electron energy spectrometer and a time-of-flight secondary ion mass analyzer for surface analysis in which the electron-energy analyzer and input lens system also serve as at least a part of the drift region of the time-of-flight mass analyzer, so that separate mass and energy analyzers do not need to be provided. In the time-of-flight mode, first-order time focusing is provided. Preferably, in this mode the charged-particle focusing means is used to produce a secondary ion image at the entrance plane of the charged-particle deflection means to improve the transmission efficiency.

For ions of any given mass-to-charge ratio, the spread in their initial energies as they enter a drift region of the time-of-flight spectrometer causes a spread in arrival times at the end of any linear portion of that drift region. However, for ions of a given mass-to-charge ratio, the faster (i.e. more energetic) ions will take longer paths through the charged-particle deflection means, so that the slowest ions will have shorter transit times through the charged particle deflection means than the faster ones. The apparatus is constructed so that the positional spread caused by different initial ion energies in the linear portion of the drift regions is compensated by the opposite effect in the charged-particle deflection means, thereby increasing the mass resolution in the secondary ion mode. According to the invention, this time focusing can be obtained in several ways:

Firstly, the relative lengths of the curved portion of the drift region (charged-particle deflection means) and the linear portion can be selected to obtain time focusing. Because the linear drift region is in practice largely comprised of the distance between the specimen and the entrance of the charged-particle deflection means, and typically comprises the charged-particle focusing means, this distance is fixed by the requirements of the electron energy spectrometer. Similarly, the dimensions of the charged-particle deflection means are determined by the need for it to serve as a high-performance electron-energy analyzer. Consequently the invention may provide time-focusing by providing a portion of the linear-drift region between the exit of the charged-particle deflection means and the charged-particle detection means, thereby providing a longer linear drift region. (In practice it is found that when the dimensions of the instrument are optimised for use as an electron spectrometer, the linear drift region is typically too short). Alternatively, it is within the scope of the invention to arrange the physical length of the charged-particle focusing means to be that required for time focusing to be obtained in the secondary ion mass spectrometer mode, and to arrange the electrostatic lens systems within it to provide proper operation in the electron-energy spectrometer mode. Unfortunately this tends to result in a physically large instrument. Secondly, and most preferably, time focusing may be achieved by provision of means to cause the ions to travel with different energies through the charged-particle deflection means and at least a pad of the linear drift means. In this way the transit times through the linear and curved portions of the drift path can be adjusted relative to one another so that time-focusing can be obtained without changing the dimensions of the apparatus. Consequently, in apparatus according to the invention time-focusing secondary ion mass spectroscopy can be achieved without any compromise to the use of the apparatus as an electron-energy spectrometer.

In practice the ions can be caused to travel through the curved and linear portions of the drift region with different energies by biasing the charged-particle deflecting means at a potential different from that at which the ions traverse at least a pad of the linear drift means. Typically, the charged-particle deflection means will comprise two curved (part-cylindrical or part-spherical) electrodes between which exists a central trajectory along which charged-particles having exactly the pass energy of the deflection means will travel. When such a deflection means is used as a conventional electron-energy analyzer it is conventional to provide means for varying the potential of the central trajectory (by adjustment of the potentials applied to the electrodes) relative to the potential at which the electrons to be analyzed are generated, but no time-of-flight mass spectrometers in which curved and linear portions of the drift region are maintained at different potentials are known.

As in any time-of-flight mass spectrometer, the irradiation means for generating secondary ions must produce bunches of ions. The apparatus therefore may comprise a pulsed primary ion beam gun which irradiates the specimen surface with bunches of primary ions to liberate bunches of secondary ions suitable for time-of-flight analysis. Typically the specimen is maintained at a high positive voltage (for example +4,000 volts) and a grounded extractor electrode is provided between a said specimen and said charged-particle focusing means to accelerate positive secondary ions to +4 keV energy. They may then transverse at least a portion of the linear drift means at ground potential and with 4 keV energy. Alternatively, the specimen may be maintained at ground potential to facilitate its heating and/or cooling and the extractor electrode maintained at either −4000 volts for positive secondary ions or +4000 volts for negative secondary ions. This requires the subsequent drift regions to be biased at ±4000 volts rather than at ground potential so that the ions traverse them with 4 keV energy, but nevertheless has advantages in some circumstances. In a further variation a continuous primary beam may be employed and the potential of the extractor electrode may be switched to interrupt the flow of secondary ions and generate the necessary ion bunches. However this method is less preferred because the primary ion beam continues to cause damage to the specimen surface in the periods when ions cannot be accepted by the time-of-flight spectrometer.

Other apparatus for generating secondary ions may also be employed. For example, one or more lasers may be used carrying out laser desorption or ablation, or the specimen may be bombarded with neutral particles. It is also within the scope of the invention to post-ionize neutral molecules or atoms sputtered from the specimen, for example by a laser directed to a region above the surface of the specimen, using either resonant or non-resonant multiphoton ionization. Ions produced by such ionization processes are regarded as secondary ions for the purposes of describing this invention.

The method of gating of the primary or secondary ion beam significantly affects performance and must be chosen with care. Many suitable arrangements are known in the art of time-of-flight mass spectrometry, for example the primary ion gun disclosed in U.S. Pat. No. 4,912,327.

In a most preferred embodiment the, charged-particle deflection means and the linear drift means of the invention may respectively comprise the hemispherical analyzer and input lens arrangement of a conventional electron energy spectrometer intended for surface analysis, as discussed previously. It will be seen that instruments of this kind can be converted to a combined electron spectrometer and secondary ion mass spectrometer with only minimal alterations to the mechanical arrangement of the apparatus.

In a yet further embodiment, apparatus according to the invention may be arranged to produce an electron image of the surface of the specimen comprising only electrons having a specified range of energies, for example as taught by European patent specification 246841 B1. Apparatus according to the invention may also be used to produce both selected energy electron images and mass-selected secondary ion images of the surface by provision of aperture means which limit the area of the surface from which ions and electrons are received and by scanning that area over the surface to be imaged to build up an image of a greater part of the surface. Such "microprobe" instruments are conventional in both electron energy spectrometers and secondary ion mass spectrometers.

The invention further provides a method of analyzing the surface of a specimen by electron spectroscopy and secondary ion mass spectrometry, said method comprising the steps of:

a) when said specimen is being analyzed by electron spectroscopy, irradiating it to cause it to emit electrons from said surface;

b) when said specimen is being analyzed by secondary ion mass spectroscopy, generating one or more bunches of secondary ions from said surface, the secondary ions comprised in each of said bunches having a spread of initial kinetic energies, and accelerating the ions comprised in each of said bunches by passing them through a potential gradient;

c) causing said electrons or said ions respectively generated in either step a) or b) to travel through:

1) one or more linear drift regions which at least some of said ions or electrons enter and leave without change in direction and in which ions in each of said bunches separate in time according to their velocities; and 2) charged-particle deflection means which said ions or electrons enter in one direction and leave in another, said deflection means having notional entrance and exit planes disposed such that an energy dispersed electron image of electrons passing through said entrance plane may be formed in said exit plane, and in which ions of a given mass-to-charge ratio in each of said bunches separate in time by virtue of the faster ions taking longer paths, and therefore having longer transit times;

d) during their passage through at least one of said linear drift regions, focusing at least said electrons to form at said entrance plane a charged-particle image of at least a pad of the surface from which they were emitted;

e) detecting said electrons or said ions after they have passed through said linear drift regions and said charged-particle deflection means and producing a signal indicative of their number;

f) when said specimen is being analyzed by secondary ion mass spectroscopy, measuring the time taken for at least some of the ions comprised in said bunches to travel through said linear drift regions and said charged-particle deflecting means, thereby determining the mass-to-charge ratio of at least some of the ions emitted from at least a part of said surface; and g) when said specimen is being analyzed by electron spectroscopy, allowing only electrons having a desired range of energies to pass through said charged-particle deflection means and to be detected, thereby determining the energy with which at least some of said electrons are emitted from said surface;

wherein when said specimen is being analyzed by secondary ion mass spectroscopy, the separation in time of ions having the same mass-to-charge ratio during their passage through said linear drift regions due to said spread of initial kinetic energies is compensated by the different times taken for ions having the same mass-to-charge ratio but different energies to travel through said charged-particle deflection means along their different paths so that ions of the same mass-to-charge ratio in each of said bunches take the same time to travel through the combination of said linear drift region and said charged-particle deflection means.

The method of the invention therefore provides a method of surface analysis incorporating both electron spectroscopy and secondary ion mass spectroscopy in which both electrons and ions pass through a single charged-particle deflection means and which is therefore simpler and cheaper to carry out than prior methods.

The method is a method of time-focusing secondary-ion mass spectroscopy and encompasses several embodiments which provide this. Firstly, the relative lengths of the linear drift regions and the charged-particle deflection means can be selected so that the compensation referred to above is obtained, in which case the electrical potential applied to the electrodes in the linear drift region will be such that ions enter and leave the region with the same energy. Secondly, the ions may be caused to travel with different energies through the charged-particle deflection means and at least a part of the linear drift region In this way the relative transit times through the linear and curved portions of the drift path can be adjusted without changing the dimensions of the apparatus. Conveniently, this may be achieved by maintaining the central trajectory of the charged-particle deflection means at a different potential from that at which the ions transverse at least a part of the linear drift means.

BRIEF DESCRIPTION OF THE DRAWINGS

A preferred embodiment of the invention, given by way of example only, will be discussed below in greater detail with reference to the figures, in which.

DESCRIPTION OF THE DISCLOSED EMBODIMENT

Figure 1:
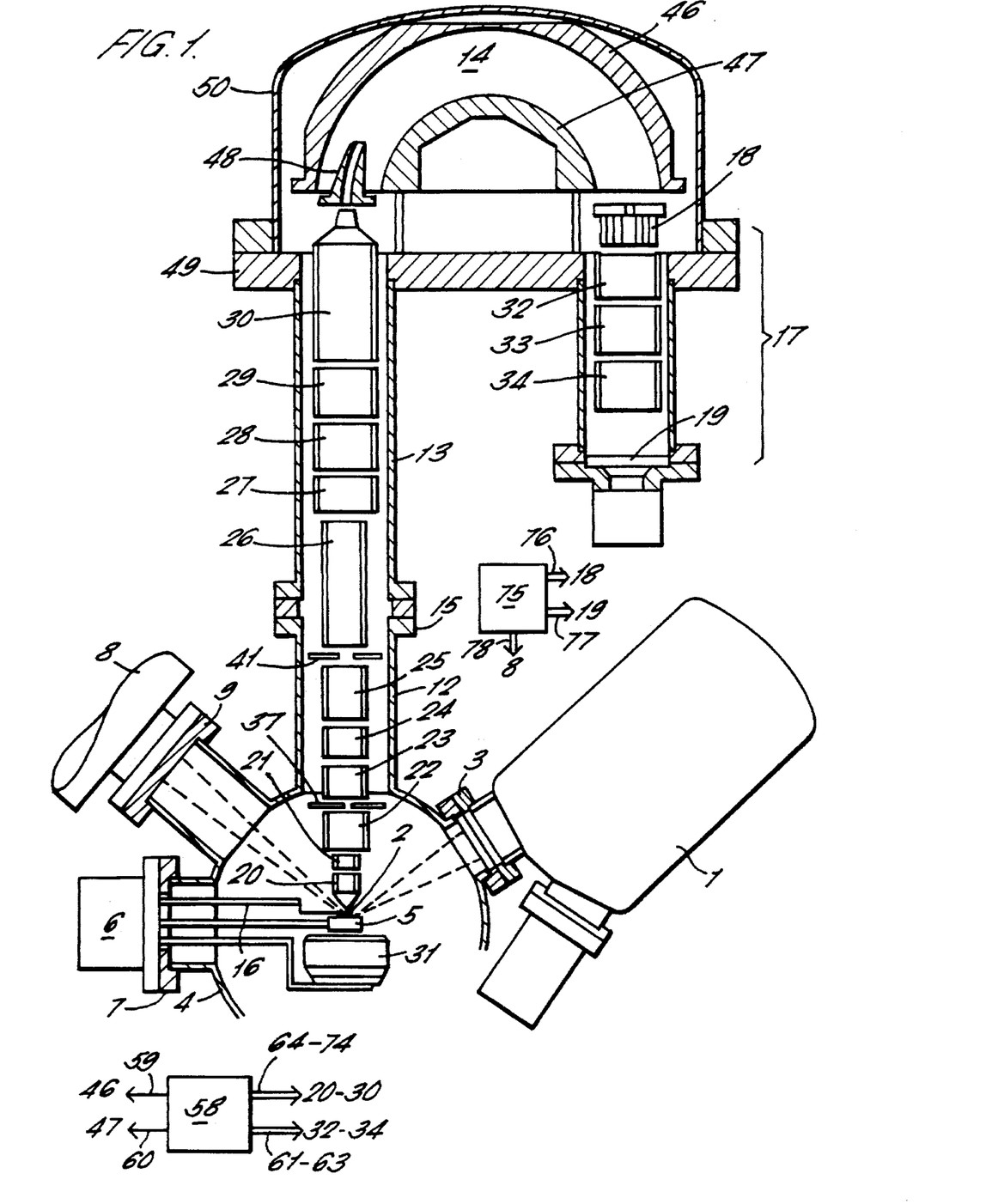
FIG. 1 is a simplified sectional view of apparatus for surface analysis according to the invention.

Referring first to FIG. 1, apparatus according to the invention comprises means for irradiating a specimen 2 to cause it to emit electrons, provided by a source of monochromatic X-rays. The source 1 irradiates an area on specimen 2 to release photoelectrons, enabling the apparatus to be used for X-ray-photoelectron spectroscopy (XPS). Source 1 is mounted on a flange 3 on a spherical vacuum housing 4 which is maintained at ultrahigh vacuum (better than $10^{-8}$ torr) by a pumping system (not shown). The specimen 2 is mounted on a holder 5 which is supported by a positioner 6 mounted on a flange 7 on the housing 4. The positioner 6 allows, by manipulation of controls outside the vacuum system, a specimen 2 to be positioned so that any part of its surface may be analyzed.

Figure 2:
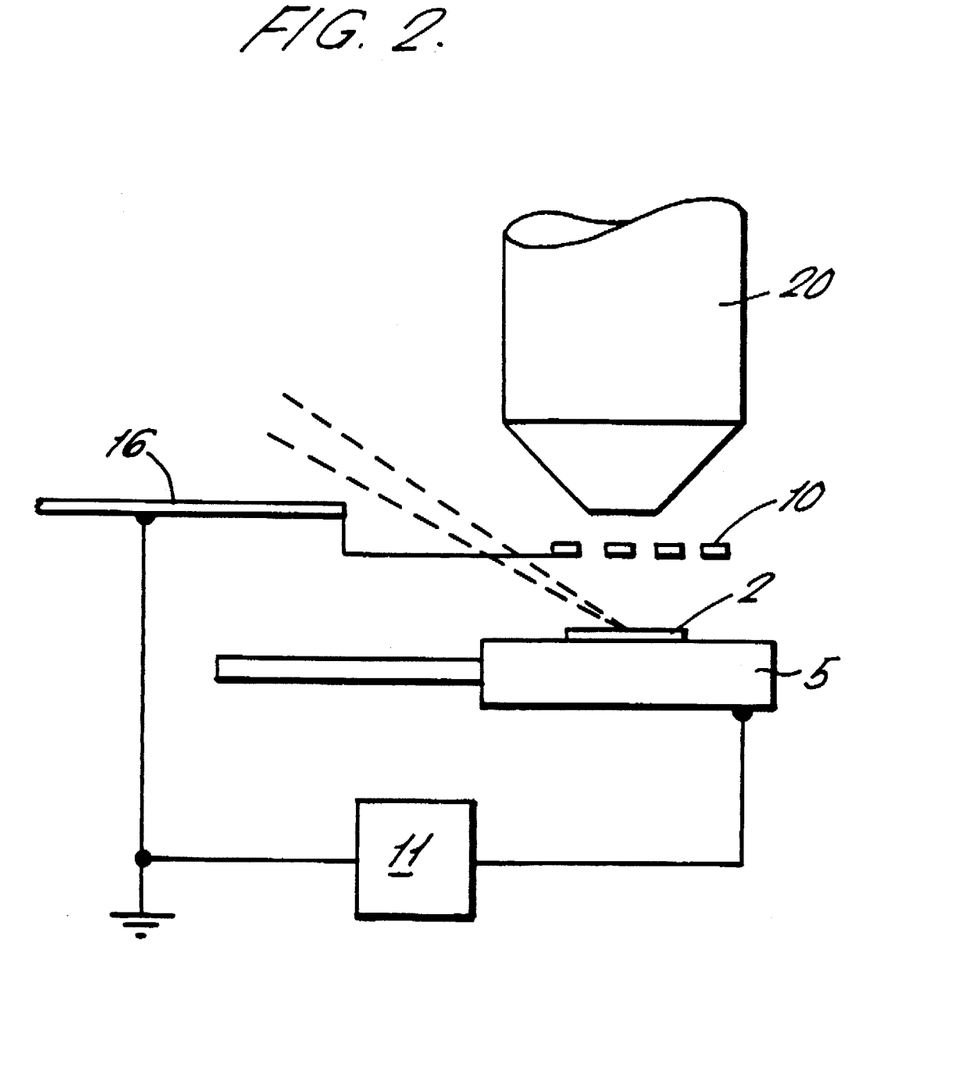
FIG. 2 is an enlarged view of part of the apparatus of FIG. 1.

Irradiation means for irradiating a specimen 2 and generating therefrom one or more bunches of secondary ions comprise a primary ion gun 8 mounted on a flange 9 on the vacuum housing 4. The gun 8 is gated to enable it to produce bunches of primary ions, typically $Ga^+$ from a liquid metal ion source, which are focused on to a small area on the surface of the specimen 2, thereby releasing from that surface bunches of secondary ions suitable for time-of-flight mass analysis. FIG. 2 illustrates the region of the specimen holder 5 in more detail and shows means for accelerating the secondary ions comprised in the bunches which comprise an extractor electrode 10 and a power supply 11 connected between it and the specimen holder 5 and the specimen 2. Conveniently, the extractor electrode 10 is grounded and specimen holder 5 is maintained at +4 kV by the power supply 11, but other potentials may be used if appropriate. In this way, bunches of secondary ions emitted from the surface of the specimen 2 in response to the bunches of primary ions from the gun 8 are accelerated through the potential gradient which exists between the extractor electrode 10 and the specimen holder 5. The extractor electrode 10 is mounted on a retractable support 16 to enable it to be withdrawn from the vicinity of the specimen when not in use. It will be appreciated that any suitable radiation source can be used in place of the gun 8 to cause secondary ions to be emitted from the surface, for example, one or more lasers for carrying out laser desorption, ablation, or multiphoton ionization experiments. Further, in the case when negative secondary ions are to be analyzed, the potential of the specimen holder 5 may be maintained at a negative potential with respect to the extractor electrode 10 by the power supply 11.

Electrons or ions emitted from the surface of the specimen 2 pass through an outlet tube 12 which is connected by a flange 15 to an input tube 13 of a charged-particle deflection means generally indicated by 14. After passing through the charged-particle deflection means 14 at least some of the electrons or ions reach a charged particle detection means generally indicated by 17, which produces an electrical signal indicative of the number of electrons or ions which enter it. The detection means 17 comprises six channel electron multipliers 18 which may serve as a conventional multi-channel detector when the apparatus is used as an electron-energy spectrometer, and a channelplate detector 19, used as an ion detector in the secondary ion mass spectrometer mode and an electron detector in certain modes of operation as an electron energy spectrometer.

Ions and electrons are conducted from the specimen 2 to the charged-particle deflection means 14 through a series of electrostatic lens elements 20–30. A single-pole magnetic lens 13 is also provided for use in certain electron-spectroscopy modes. Three further lens elements 32–34 are between the charged-particle deflection means 14 and the channelplate detector 19.

Figure 3:
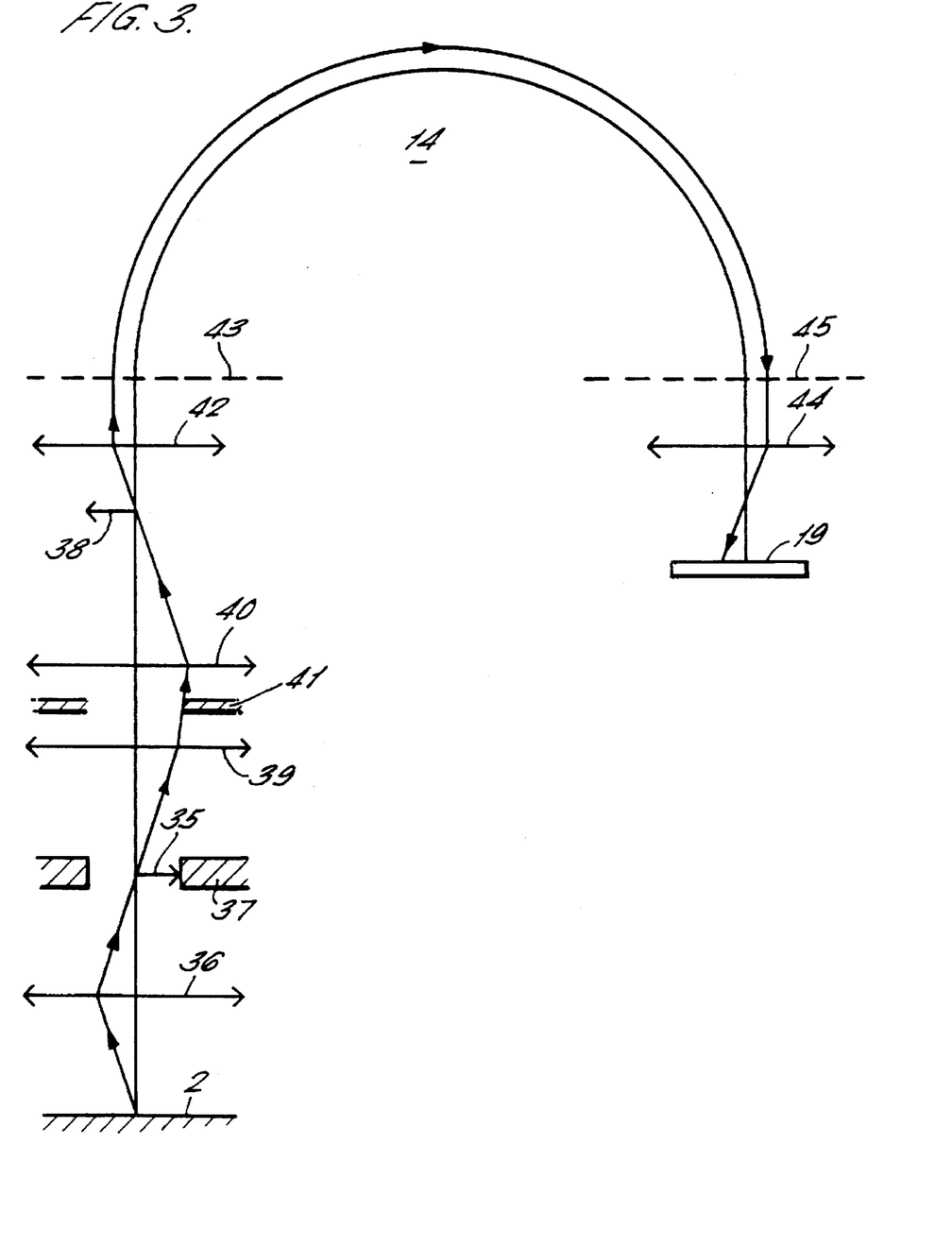
FIG. 3 is a simplified diagram of the optical arrangement of the apparatus of FIG. 1 used as an electron energy spectrometer.

FIG. 3 is a simplified diagram of an optical arrangement which may be employed when the apparatus is used as an electron spectrometer. An electron image of the surface of the specimen 2 is formed by the first lens 36 which comprises the electrostatic lens elements 20–22, the magnetic lens 31, or both the electrostatic lens and magnetic lens acting together. The image 35 is formed in the plane of an adjustable aperture 37, the size of which can be adjusted to determine the area of the specimen surface from which electrons are collected. A second electron image 38 is formed by the second lens 39 comprising electrostatic elements 23–25, and an adjustable aperture 41 is provided between them for adjusting the collection angle. A third lens 42, comprising the electrostatic lens elements 26–30 is positioned at its focal length from the electron image 38 and so that its back focal plane is coincident with the entrance plane 43 of the charged particle deflection means 14, and a fourth lens 44 comprising electrostatic lens elements 32–34 is similarly positioned with respect to the exit plane 45 of the charged-particle deflection means 14. In this way an energy-filtered electron image of the specimen surface is formed in the plane of the channelplate detector 19, while an electron energy spectrum of a selected area of the specimen can be simultaneously recorded on the exit plane 45 by means of the channel electron multipliers 18 whose entrances are located in this plane. The combined mode of imaging and spectral recording made possible by the combination of the lenses 42 and 44 with a charged-particle deflection means comprising a hemispherical analyzer is discussed in detail in patent specification EP 246841 but is not an essential feature of the present invention. For example as an alternative the lenses may be adjusted so that the electron image 38 is formed in the entrance plane 43, providing a more conventional mode of operation. Further, as in a conventional electron-energy spectrometer, electrons leaving the specimen 2 may be retarded to increase the energy resolution of the charged-particle deflection means, typically by maintaining the electrostatic lens element 27, and all subsequent elements, at a potential different from that of the specimen 2, thereby changing the kinetic energy of the electrons before and during their passage through the charged-particle deflection means.

The charged-particle deflection means 14 is a conventional analyzer comprising two hemispherical electrodes 46, 47 and is shown only schematically in FIG. 1. It has notional entrance and exit planes (43, 45 respectively) which are such that an energy dispersed image of electrons passing through the entrance plane 43 is formed in the exit plane 45 and is fitted with an $\alpha$-angle restrictor 48 to restrict the angular spread of the electron beam as it enters the analyzer. The electrodes 46, 47 are supported from a base plate 49 and fitted with a cover 50. There are no features of the analyzer 14 which distinguish it from the prior types conventionally used for electron spectroscopy.

Figure 4:
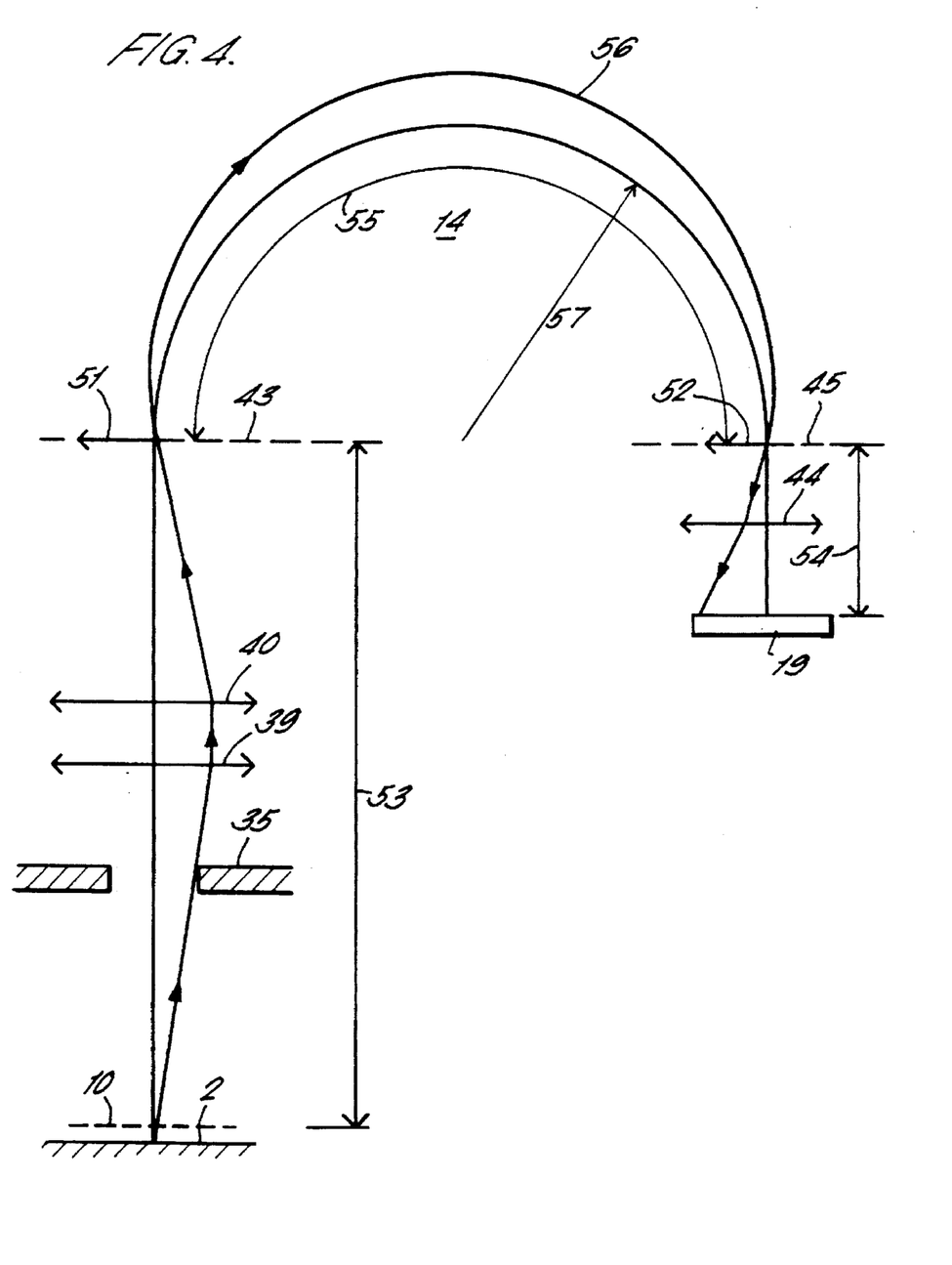
FIG. 4 is a simplified diagram of the optical arrangement of the apparatus of FIG. 1 used as a secondary-ion time-of-flight mass spectrometer.

FIG. 4 is a diagram of the optical arrangement of the apparatus when used for secondary ion time-of-flight mass spectrometry. As explained, secondary ions emitted from the surface of the specimen 2 are accelerated by the accelerating electrode 10 and focused to form a secondary ion image 51 in the entrance plane 43 of the charged-particle deflection means 14 by means of the electrostatic lens elements 20–30 which are denoted in FIG. 4 as the first, second and third lenses 36, 39 and 42 (for consistency with FIG. 3). The adjustable aperture 35 now serves as a collection angle defining aperture. The charged-particle deflection means 14 now produces In the exit plane 45 an image 52 of the secondary ion image 51, and the fourth lens 44 (comprising electrostatic lens elements 32–34) is used to defocus this image and transmit it on to the channelplate multiplier 19. Lens 44 is used in this way to minimize damage to the detector which may otherwise result if a focused secondary ion image was formed on its surface. The channel electron multipliers 18 are not preferred for use in the secondary ion mode because the geometry of their entrances does not define a plane surface and their use would therefore produce a variation in the flight time depending on the position at which ions strike them.

The flight path of the time-of-flight mass spectrometer therefore comprises a first linear drift region 53, a second linear drift region 54 and a curved drift region including the charged-particle deflection means 14, typified by the trajectory 56.

As in a conventional time-of-flight mass spectrometer, ion bunches accelerated by the extractor electrode 10 will separate in time according to their velocities in both the first and second linear drift regions 53 and 54, and, as the extractor electrode 10 provides all the ions in each bunch with the same additional kinetic energy, ions of different mass-to-charge ratio are therefore separated in time. As explained, this separation is blurred by the spread in initial kinetic energies which exists for ions of any given mass-to-charge ratio at the moment of their formation on the surface of the specimen 2. According to the invention, the effect of this energy spread is reduced by the inclusion in the flight path of the charged-particle deflection means 14, during their passage through which ions will travel along trajectories of different lengths according to their initial velocity. Thus, by proper selection of the relative length of the linear drift regions 53 and 54 and the path length 55 of the charged particle deflecting means, the separation in time of ions having the same mass-to-charge ratio which occurs during their passage through linear drift regions due to the spread in initial kinetic energies may be compensated by the different times taken for those ions to travel through the charged particle deflecting means along their different trajectories. Put simply, ions which have the highest kinetic energy arrive soonest at the entrance plane 43 but are subsequent delayed as they take a greater radius (and therefore longer) path through the charged-particle deflecting means 14. By proper selection of the relative lengths of the drift regions 53 and 54, all ions of a given mass-to-charge ratio can be made to arrive simultaneously at the channelplate detector 19.

According to the invention this time-focusing action can be obtained by adjustment of the lengths of the various portions of the apparatus, but because the lengths 53 and 54 are typically determined by the requirements of the electron spectroscopy mode illustrated in FIG. 3 it is unlikely that accurate time-focusing can be obtained with the lengths optimised for that mode.

Consequently, the ions are either accelerated (or retarded, as necessary) before they enter the charged-particle deflection means but after they have traversed most of the linear drift region. This is done by maintaining a potential difference between the final electrostatic lens element 30 of the third lens 42 and all the subsequent elements, including the restrictor 48 and the hemispherical electrodes 46 and 47 but not necessarily the elements 32–34 which comprise the fifth lens 44. In this way the kinetic energy of the ions is either increased (or decreased) for their passage through the charged-particle deflection means, so that their relative flight times through the linear drift means 53 and the charged-particle deflection means can be adjusted to obtain time-focusing, even though the relative physical lengths may not be correct.

The symbols used in the following have the meanings set out below:

$R_0$: radius (57) of the central trajectory of the charged-particle deflecting means 14.

$E_p$: pass energy of the charged-particle deflecting means 14.

$V_0$: bias voltage applied to the specimen 2.

$E_0$: energy of ions emitted from the specimen 2 ($=eV_0$)

$E_r$: reference energy of the charged-particle deflecting means 14 ($=E_0-E_p$)

$d_1$: portion of linear drift regions 53, 54 which are maintained at ground potential so that the ions transverse them with energy $E_0$;

$d_2$: portion of the linear drift regions 53, 54 which are maintained at the analyzer retard potential so that the ions transverse them with energy $E_p=(E_0-E_r)$;

$d_i$: various lengths corresponding to portions of the linear drift regions 53, 54 within the lenses maintained at potential $V_i$; which the ions transverse with energy $E_i=e(V_0-V_i)$.

From the simple relationships $E=\frac{1}{2}mv^2$ and $t=d/v$, the flight time through each of the regions defined above.

$$t = \sqrt{\frac{m}{2E}}\ d$$

where d equals $d_1$, $d_2$, $d_i$ or, for the analyzer, $\pi R_0$. The total flight time through the analyzer for ions of energy $E_0$ is therefore given by $$t = \sqrt{\frac{m}{2}}\left\{\frac{d_1}{\sqrt{E_O}} + \frac{d_2 + \pi R_0}{\sqrt{E_p}} + \sum_i \frac{d_i}{\sqrt{E_i}}\right\}$$

Some ions emitted from the sample surface will have an energy $E=E_0+\Delta E$ which can be expressed as $E_0(1+\delta)$, where $\delta=\Delta E/E_0$. It can be shown that for a hemispherical analyzer the length R of the semi-major axis of the resulting elliptical path is given by $$R = R_0\left(1 + \frac{\delta E_O}{E_p}\right)$$

and that the transit time of these ions through the analyzer will be proportional to $(R/R_0)^{3/2}$. The total flight time through the analyzer of ions of energy E is therefore given by:

$$t = \sqrt{\frac{m}{2}}\left\{\frac{d_1}{\sqrt{E_O}}(1+\delta)^{-1/2} + \frac{d_2}{\sqrt{E_p}}\left(1+\frac{\delta E_O}{E_p}\right)^{-1/2} + \frac{\pi R_0}{\sqrt{E_p}}\left(1+\frac{\delta E_O}{E_p}\right)^{3/2} + \sum_i \frac{d_i}{\sqrt{E_i}}\left(1+\frac{\delta E_O}{E_I}\right)^{-1/2}\right\}$$

For first order time focusing (as described above) to be obtained, $$\left(\frac{dt}{d\delta}\right)_{\delta=0} = 0$$

Differentiation and rearrangement, substituting $\delta=0$ gives $$d_1 E_O^{-3/2} + (d_2 - 3\pi R_0)E_p^{-3/2} + \sum_i d_i E_i^{-3/2} = 0$$

This equation can be used to calculate the value of $E_p$ (and hence the analyzer retard potential) which is required to achieve first-order time focusing for any given geometrical arrangement. For example, in a simple case when the input lenses are not used to form a secondary ion image of the surface on the entrance plane 43, $d_i=0$ and the equation simplifies to $$\frac{E_p}{E_O} = \left(\frac{3\pi R_0 - d_2}{d_1}\right)^{2/3}$$

In a practical embodiment $d_1=0.8$ m, $d_2=0.29$ m, $R_0=0.15$ m, so that $E_p=1.25\ E_0$, which means that ions are accelerated into the analyzer because for these dimensions the curved drift region is too long relative to the linear drift region. With other geometrical arrangements, however, it may be necessary to retard the ions rather than to accelerate them.

When, as is preferred, input lenses are used in retarding mode to focus the ions on to the entrance slit of the analyzer, $d_i \neq 0$ and the value of $E_p/E_0$ will typically be decreased. In practice the optimum condition for time focusing in these circumstances should be found by experiment because it is difficult to measure $d_i$ precisely, and for the instrument specified above the optimum value of $E_p/E_0$ was found to be approximately 1.09 when focusing was employed.

Suitable voltages are applied to each of the electrostatic lens elements 20–30, 32–34, and the electrodes 46,47 of the charged-particle deflection means 14, by a switchable power supply means 58 (FIG. 1) by means of the electrical leads 59–74. These leads are connected to the lens elements and electrodes via electrical feedthroughs (not shown) in the vacuum housing. The power supply 58, which is advantageously computer controlled, provides all the potentials required for operation of the apparatus as an electron-energy spectrometer as discussed, and, when required, potentials of the reverse polarity for operation as a positive secondary-ion mass spectrometer. In the electron-spectrometer mode, the potentials supplied to the electrodes 46 and 47 are such that an energy dispersed electron image is formed either on the exit plane 45 (in which the entrances of the channel electron multipliers 18 are disposed) or on the channelplate multiplier 19, thereby providing means for allowing only electrons having a certain range of energies to reach the charged-particle detection means 17. A data-processing means 75 receives signals from the multipliers 18 and 19 via the electrical leads 76, 77, allowing the determination of the energy at which at least some electrons leave the surface of the specimen 2.

In the secondary ion mass spectrometry mode, the data-processing means 75 also controls the primary ion gun 8, via the lead 78, to produce bunches of primary ions at predetermined time intervals, as in a conventional time-of-flight secondary ion mass spectrometer. Means 75 incorporates means for measuring the time taken for each of the secondary ions released by each primary ion bunch to travel to the channelplate detector 19, thereby providing a measure of their mass-to-charge ratio.

We claim:

1. Apparatus for the analysis of a surface of a specimen by electron spectroscopy and secondary ion mass spectrometry, said apparatus comprising:
   a) first irradiation means for irradiating a specimen to cause said specimen to emit electrons from a surface;
   b) second irradiation means for irradiating said specimen and generating therefrom one or more bunches of secondary ions, the secondary ions in each of said bunches having a spread of initial kinetic energies;
   c) means for accelerating said secondary ions by passing said secondary ions through a potential gradient;
   d) charged-particle detection means for producing an electrical signal indicative of the number of said emitted electrons or said secondary ions which impinge thereon;
   e) disposed between said specimen and said charged-particle detection means:
      1) means defining one or more linear drift regions which at least some of said electrons, or said ions after passing through said potential gradient, enter and leave without change in direction and in which ions in each of said bunches separate in time according to their velocities; and
      2) charged-particle deflection means which charged-particles enter in one direction and leave in another direction, said deflection means having notational entrance and exit planes disposed such that an energy-dispersed electron image of electrons passing through said entrance plane is formed in said exit plane, and in which ions of a given mass-to-charge ratio in each of said bunches separate in time by virtue of the faster ions taking longer paths and therefore having longer transit times, said deflection means including electrodes;

f) charged-particle focusing means for transmitting said electrons or said ions through at least one of said linear drift regions so that at least when electrons are being transmitted a charged-particle image of at lest a part of said surface from which said electrons are emitted is formed at said entrance plane, said focusing means including electrodes;

g) switchable power supply means for supplying electrical potentials to at least some of said electrodes of said charged-particle deflection means and said charged-particle focusing means to enable said deflection means and said focusing means to transmit ions or electrons as required;

h) means, operable when said charged-particle deflection means and said charged-particle focusing means are transmitting ions, for measuring the time taken for each of said ions comprised in said bunches to travel to said charged-particle detection means, thereby determining the mass-to-charge ratio of at least some of the ions emitted from at least a part of said surface; and i) lens means, operable when said charged-particle deflection means and said charged-particle focusing means are transmitting electrons, for allowing only electrons having a desired range of energies to reach said charged-particle detection means, thereby determining the energy at which at least some of the electrons are emitted from said specimen;

said apparatus being so arranged that the separation in time of ions having the same mass-to-charge ratio during their passage through said linear drift region, due to said spread in initial kinetic energies, is compensated by the different times taken for ions having the same mass-to-charge ratio but different energies to travel through said charged-particle deflection means along their different paths, so that ions of the same mass-to-charge ratio in each of said bunches arrive at said charged-particle detector at the same time.

2. Apparatus as claimed in claim 1 wherein said first irradiation means, charged-particle detection means, linear drift region defining means, deflection means, focusing means, power supply means and said lens means cooperate to define an electron energy spectrometer and wherein said second irradiation means, means for accelerating, detection means, drift region defining means, deflection means, focusing means, power supply means and means for measuring time cooperate to define a secondary ion time-of-flight mass spectrometer which provides time-focusing of the secondary ions.

3. Apparatus as claimed in claim 2 wherein said charged-particle focusing means produces a secondary ion image in the entrance plane of said charged-particle deflection means.

4. Apparatus as claimed in claim 2 wherein said charged-particle deflection means and said linear drift region are dimensioned so that the relative lengths of the paths taken by ions passing therethrough is such that first-order time-focusing of said secondary ions is obtained.

5. Apparatus as claimed in claim 2 further comprising means for causing said secondary ions to travel with different energies through said charged-particle defection means and said linear drift region and wherein said different energies are selected to obtain first-order time-focusing.

6. Apparatus as claimed in claim 5 wherein said electrodes comprising said charged-particle deflection means are electrically biased to potentials such that the potential of a central trajectory between said electrodes along which travel charged particles having exactly the pass energy of said charged-particle deflection means differs from the potential at which the charged-particles traverse at least a part of said linear drift region.

7. Apparatus as claimed in claim 2 wherein said irradiation means comprises a pulsed primary ion beam gun and an extractor electrode, said extractor electrode being positioned between said specimen and said charged-particle focusing means.

8. Apparatus as claimed in claim 7 wherein said extractor electrode is electrically grounded when said charged-particle deflection means is transmitting ions.

9. Apparatus as claimed in claim 2 wherein said charged-particle deflection means comprises a hemispherical charged-particle energy analyzer.

10. A method of selectively analyzing the surface of a specimen by electron spectroscopy or secondary ion mass spectrometry, said method comprising the steps of:

a) when said specimen is being analyzed by electron spectroscopy, irradiating a surface of said specimen, to cause the emission of electrons from said surface;

b) when said specimen is being analyzed by secondary ion mass spectroscopy, generating one or more bunches of secondary ions from said surface, the secondary ions comprised in each of said bunches having a spread of initial kinetic energies, and accelerating the ions comprised in each of said bunches by passing said secondary ions through a potential gradient; p1 c) causing said emitted electrons or said secondary ions to travel through:

1) one or more linear drift regions which at least some of said ions or electrons enter and leave without change in direction and in which ions in each of said bunches separate in time according to their velocities; and 2) charged-particle deflection means which said ions or electrons enter in one direction and leave in another direction, said deflection means having national entrance and exit planes disposed such that an energy dispersed electron image of electrons passing through said entrance plane is formed in said exit plane, and in which ions of a given mass-to charge ration in each of said bunches separate in time by virtue of the faster secondary ions taking longer paths;

d) during their passage through at least one of said linear drift regions, focusing at least said electrons to form at said entrance plane a charged-particle image of at least a part of said surface from which they were emitted;

e) detecting said electrons or said ions after they have passed through said linear drift regions and said charged-particle deflection means and producing a signal indicative of their number;

f) when said specimen is being analyzed by secondary ion mass spectroscopy, measuring the time taken for at least some of the ions comprised in said bunches to travel through said linear drift regions and said charged-particle deflecting means, thereby determining the mass-to-charge ratio of at least some of the ions emitted from at least a part of said surface; and g) when said specimen is being analyzed by electron spectroscopy, allowing only electrons having a desired range of energies to pass through said charged-particle deflection means and to be detected, thereby determining the energy with which at least some of said electrons are emitted from said surface;

wherein when said specimen is being analyzed by secondary ion mass spectroscopy, the separation in time of ions having the same mass-to-charge ratio during their passage through said linear drift regions due to said spread of initial kinetic energies is compensated by the different times taken for ions having the same mass-to-charge ratio but different energies to travel through said charged-particle deflection means along their different paths so that ions of the same mass-to-charge ration in each of said bunches take the same time to travel through the combination of said linear drift region and said charged-particle deflection means.

11. A method as claimed in claim 10 wherein the relative lengths of the linear drift region and the charged-particle deflection means are so dimensioned that the relative lengths of the paths taken by said secondary ions is such that first-order time focusing of said secondary ions is obtained.

12. A method as claimed in claim 10 further comprising the step of causing said secondary ions to travel with different energies through the charged-particle deflection means and at least a part of the linear drift region, said different energies of said secondary ions being selected to obtain first-order time focusing.

* * * * *